US012544059B2

(12) United States Patent
Umar et al.

(10) Patent No.: US 12,544,059 B2
(45) Date of Patent: Feb. 10, 2026

(54) RETENTION SUTURE ASSEMBLY

(71) Applicant: Sanusi Umar, Manhattan Beach, CA (US)

(72) Inventors: Sanusi Umar, Manhattan Beach, CA (US); Andrew Namminga, Austin, TX (US)

(73) Assignee: Sanusi Umar, Manhattan Beach, CA (US)

( * ) Notice: Subject to any disclaimer, the term of this patent is extended or adjusted under 35 U.S.C. 154(b) by 53 days.

(21) Appl. No.: 18/751,490

(22) Filed: Jun. 24, 2024

(65) Prior Publication Data

US 2024/0366209 A1 Nov. 7, 2024

Related U.S. Application Data

(60) Division of application No. 18/110,411, filed on Feb. 16, 2023, now Pat. No. 12,042,140, which is a division of application No. 16/721,794, filed on Dec. 19, 2019, now Pat. No. 11,607,212, which is a continuation-in-part of application No. PCT/US2019/023188, filed on Mar. 20, 2019.

(60) Provisional application No. 62/645,798, filed on Mar. 21, 2018.

(51) Int. Cl.
*A61B 17/04* (2006.01)

(52) U.S. Cl.
CPC .. *A61B 17/0401* (2013.01); *A61B 2017/0459* (2013.01)

(58) Field of Classification Search
CPC .................... A61B 17/0401; A61B 2017/0495
See application file for complete search history.

(56) References Cited

U.S. PATENT DOCUMENTS

| | | | |
|---|---|---|---|
| 2,199,025 | A | 4/1940 | Conn |
| 3,664,345 | A | 5/1972 | Dabbs et al. |
| 4,210,148 | A | 7/1980 | Stivala |
| 4,896,668 | A | 1/1990 | Popoff |
| 5,009,663 | A | 4/1991 | Broome |
| 5,127,412 | A | 7/1992 | Cosmetto |
| 5,464,426 | A | 11/1995 | Bonutti |
| 6,120,525 | A | 9/2000 | Westcott |

(Continued)

FOREIGN PATENT DOCUMENTS

| | | |
|---|---|---|
| CN | 205866896 | 1/2017 |
| FR | 2453632 | 11/1980 |

*Primary Examiner* — Phong Son H Dang
(74) *Attorney, Agent, or Firm* — Millen, White, Zelano & Branigan, P.C.; Christopher W. Brody

(57) ABSTRACT

This invention relates to devices that join a pair of edges. Previously, suture assemblies used holes perpendicular to a vertical plane. Embodiments of the present invention use a first pad tunnel (130) between a first pad lower plane opening (126) and a first pad upper plane opening (122). A first pad tunnel major axis (132) passes through a first pad upper plane opening center (124) and a first pad lower plane opening center (128). For reference a first pad orthogonal axis (134) passes through the first pad upper plane opening center (124) orthogonal to the first pad upper plane (118) and the first pad lower plane (120). A first pad angle ($\theta 1$) is measured clockwise from the first pad orthogonal axis (134) to the first pad tunnel major axis (132). The first pad angle is at least five degrees but no more than 175 degrees.

8 Claims, 21 Drawing Sheets

(56) References Cited

U.S. PATENT DOCUMENTS

| | | | | |
|---|---|---|---|---|
| 7,396,359 | B1 * | 7/2008 | Derowe ................ | A61B 17/11<br>606/213 |
| 9,034,012 | B2 | 5/2015 | Knoell | |
| 10,123,801 | B2 | 11/2018 | Belson | |
| 10,159,825 | B2 | 12/2018 | Belson | |
| 10,456,136 | B2 | 10/2019 | Belson | |
| 2012/0290002 | A1 | 11/2012 | Astorino | |
| 2013/0197580 | A1 | 8/2013 | Perriello | |
| 2015/0272558 | A1 | 10/2015 | Smith | |

* cited by examiner

RETENTION SUTURE ASSEMBLY

RELATED APPLICATION

This application is a Divisional of U.S. application Ser. No. 18/110,411 filed on Feb. 16, 2023, which is a Divisional of U.S. application Ser. No. 16/721,794 filed on Dec. 12, 2019, which is a continuation-in-part of international patent application PCT/US2019/023188 filed on Mar. 20, 2019. The '188 application claims priority to provisional patent application U.S. Ser. No. 62/645,798 filed on Mar. 21, 2018, the entire contents of both applications is herein incorporated by reference.

BACKGROUND

The embodiments herein relate generally to systems to close and heal wounds.

Prior to embodiments of the disclosed invention retention suture assemblies had holes that were perpendicular to the plane of the plates. Some examples of this are shown in U.S. Pat. No. 4,210,148 issued to Stivala, U.S. Pat. No. 6,120,525 issued to Westcott, and U.S. Pat. No. 5,127,412 issued to Cosmetto. Of those, Stivala is the most widely used and is described in FIG. 1.

FIG. 1 shows a wound W that is in skin S. There is a first suture assembly 1 that further comprises a first pad 2 joined to a first plate 3. A first pad hole 4 and a first plate hole 5 are linearly aligned, a first suture assembly 1 that further comprises a first pad 2 joined to a first plate 3. There is a second suture assembly 6 that further comprises a second pad 7 joined to a second plate 8. A second pad hole 9 and a second plate hole 10 are linearly aligned. A suture 11 travels through the first pad hole 4, the first plate hole 5, the second plate hole 9 and the second pad hole 10 perpendicular to the skin S.

The suture 11 creates two sets of forces. A closure force 12, 13 is shown pushing a first edge 14 of wound W toward a second edge 15 of wound W. The closure force 12, 13, shown in the x-direction is a good thing. However, a tearing force 16, 17 causes the suture 11 to tear through the skin S causing significant scaring. The tearing force 16, 17 is shown in the positive y-direction and is a bad thing. Embodiments of the disclosed invention solve this problem.

SUMMARY

A retention suture assembly is adapted to join a pair of edges from a wound The retention suture assembly comprises a first suture assembly, arranged proximate a first edge. The first suture assembly further comprises a first retaining bar, further comprising a first retaining bar outer perimeter, a first retaining bar upper plane and a first retaining bar lower plane. A first retaining bar upper opening further comprises a first retaining bar upper opening center and a first retaining bar lower opening further comprises a first retaining bar lower opening center. The first retaining bar lower opening center is relatively distant the first edge and the first retaining bar upper opening center is relatively proximate the first edge.

Similarly, a second suture assembly is arranged proximate a second edge and further comprises a second retaining bar, further comprising a second retaining bar outer perimeter, a second retaining bar upper plane and a second retaining bar lower plane. A second retaining bar upper opening further comprises a second retaining bar upper opening center and a second retaining bar lower opening further comprises a second retaining bar lower opening center. The second retaining bar lower opening center is relatively distant the second edge and the second retaining bar upper opening center is relatively proximate the second edge.

A suture joins the first suture assembly and the second suture assembly under tension. In some embodiments, the suture is tied into a knot. In other embodiments, the suture is tightened with a tensioning device.

In some embodiments an upper linear distance measured from the first retaining bar upper opening center to the second retaining bar upper opening center is less than a lower liner distance measured from the first retaining bar lower opening center to the second retaining bar lower opening center.

In some embodiments, the first suture assembly further comprises a first retaining bar tunnel, joining the first retaining bar upper opening and the first retaining bar lower opening; wherein the first retaining bar tunnel further comprises a first retaining bar side wall.

Similarly, the second suture assembly further comprises a second retaining bar tunnel, joining the second retaining bar upper opening and the second retaining bar lower opening; wherein the second retaining bar tunnel further comprises a second retaining bar side wall.

It follows that the suture is arranged through the first retaining bar tunnel such that the suture contacts the first retaining bar side wall distributing some of a force from the suture into the first retaining bar; the suture further arranged through the second retaining bar tunnel such that the suture contacts the second retaining bar side wall distributing some of the force from the suture into the second retaining bar pulling the first retaining bar to the second retaining bar.

A first retaining bar orthogonal axis, that is orthogonal to the first retaining bar upper plane and the first retaining bar lower plane, travels through the first retaining bar upper opening center. A first retaining bar tunnel axis travels through the first retaining bar upper opening center and the first retaining bar lower opening center. A first angle is measured clockwise from the tunnel axis to the first retaining bar orthogonal axis. The first angle is at least five degrees but no more than one hundred seventy-five degrees angled toward the first edge.

Similarly, a second retaining bar orthogonal axis, that is orthogonal to the second retaining bar upper plane and the second retaining bar lower plane, travels through the second retaining bar upper opening center. A second retaining bar tunnel axis travels through the second retaining bar upper opening center and the second retaining bar lower opening center. A second angle is measured counter clockwise from the tunnel axis to the second retaining bar orthogonal axis; wherein the second angle is at least five degrees but no more than one hundred seventy-five degrees angled toward the second edge.

A first retaining bar second upper opening further comprising a first retaining bar second upper opening center and a first retaining bar second lower opening further comprising a first retaining bar second lower opening center. The first retaining bar second lower opening center is relatively distant the first edge and the first retaining bar second upper opening center is relatively proximate the first edge.

A first retaining bar upper channel arranged into the first retaining bar upper plane and connecting the first retaining bar upper opening to the first retaining bar second upper opening; wherein the first retaining bar upper channel further comprises a first retaining bar upper channel central axis A first retaining bar central opening, spanning two sides of the first retaining bar outer perimeter creating a first retaining bar lower tunnel having a first retaining bar lower tunnel central axis wherein the first retaining bar upper channel central axis is approximately perpendicular to the first retaining bar lower tunnel central axis.

A first foot extends from the first retaining bar lower plane between a first retaining bar first edge and the first retaining bar lower opening. A second foot extends from the first retaining bar lower plane between the first retaining bar lower opening and the first retaining bar central opening. A third foot extends from the first retaining bar lower plane between the first retaining bar central opening and the first retaining bar second opening. A fourth foot extends from the first retaining bar lower plane between the first retaining bar second opening and a first retaining bar second edge.

A central portion exists between the second foot and the third foot. In some embodiments the central portion is arched away from the second foot and the third foot in a concave manner. In some embodiments this arch makes the first retaining bar upper plane convex. In other embodiments, the arch does not affect the first retaining bar upper plane. In some embodiments a through connects the first retaining bar upper plane central opening and the second retaining bar upper plane central opening.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 2:
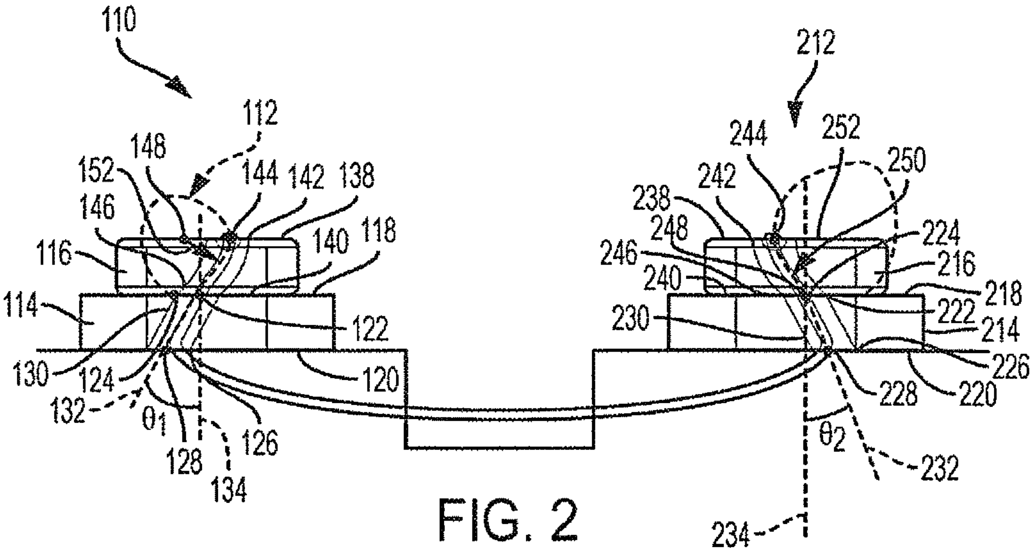
FIG. 2 shows a side section view of one embodiment of the present invention.

By way of example, and referring to FIG. 2, one embodiment of a retention suture assembly 110 further comprises a first suture assembly 112 which contains a first pad 114 adjacent to a first plate 116. The first pad 114 is bound by a first pad upper plane 118 and a first pad lower plane 120. The first pad upper plane 118 further comprises a first pad upper plane opening 122 which has a first pad upper plane opening center 124. Similarly, the first pad lower plane 120 further comprises a first pad lower plane opening 126 which has a first pad lower plane opening center 128. A first pad tunnel 130 exists between the first pad lower plane opening 126 and the first pad upper plane opening 122. A first pad tunnel major axis 132 passes through the first pad upper plane opening center 124 and the first pad lower plane opening center 128. For reference a first pad orthogonal axis 134 passes through the first pad upper plane opening center 124 orthogonal to the first pad upper plane 118 and the first pad lower plane 120. A first pad angle θ1 is measured clockwise from the first pad orthogonal axis 134 to the first pad tunnel major axis 132.

The first plate 116 is bound by a first plate upper plane 138 and a first plate lower plane 140. The first plate upper plane 138 further comprises a first plate upper plane opening 142 which has a first plate upper plane opening center 144. Similarly, the first plate lower plane 140 further comprises a first plate lower plane opening 146 which has a first plate lower plane opening center 148. A first plate tunnel 150 exists between the first plate lower plane opening 146 and the first plate upper plane opening 142. A first plate tunnel radius 152 passes through the first plate upper plane opening center 144 and the first plate lower plane opening center 148. Note that the first plate lower plane opening center 148 is adjacent to the first pad upper plane opening center 124.

Additionally, the retention suture assembly 110 further comprises a second suture assembly 212 which contains a second pad 214 adjacent to a second plate 216. The second pad 214 is bound by a second pad upper plane 218 and a second pad lower plane 220. The second pad upper plane 218 further comprises a second pad upper plane opening 222 which has a second pad upper plane opening center 224. Similarly, the second pad lower plane 220 further comprises a second pad lower plane opening 226 which has a second pad lower plane opening center 228. A second pad tunnel 230 exists between the second pad lower plane opening 226 and the second pad upper plane opening 222. A second pad tunnel major axis 232 passes through the second pad upper plane opening center 224 and the second pad lower plane opening center 228. For reference a second pad orthogonal axis 234 passes through the second pad upper plane opening center 224 orthogonal to the second pad upper plane 218 and the second pad lower plane 220. A second pad angle θ2 is measured counterclockwise from the second pad orthogonal axis 234 to the second pad tunnel major axis 232.

The second plate 216 is bound by a second plate upper plane 238 and a second plate lower plane 240. The second plate upper plane 238 further comprises a second plate upper plane opening 242 which has a second plate upper plane opening center 244. Similarly, the second plate lower plane 240 further comprises a second plate lower plane opening 246 which has a second plate lower plane opening center 248. A second plate tunnel 250 exists between the second plate lower plane opening 246 and the second plate upper plane opening 242. A second plate tunnel radius 252 passes through the second plate upper plane opening center 244 and the second plate lower plane opening center 248. Note that the second plate lower plane opening center 248 is adjacent to the second pad upper plane opening center 224.

Figure 3:
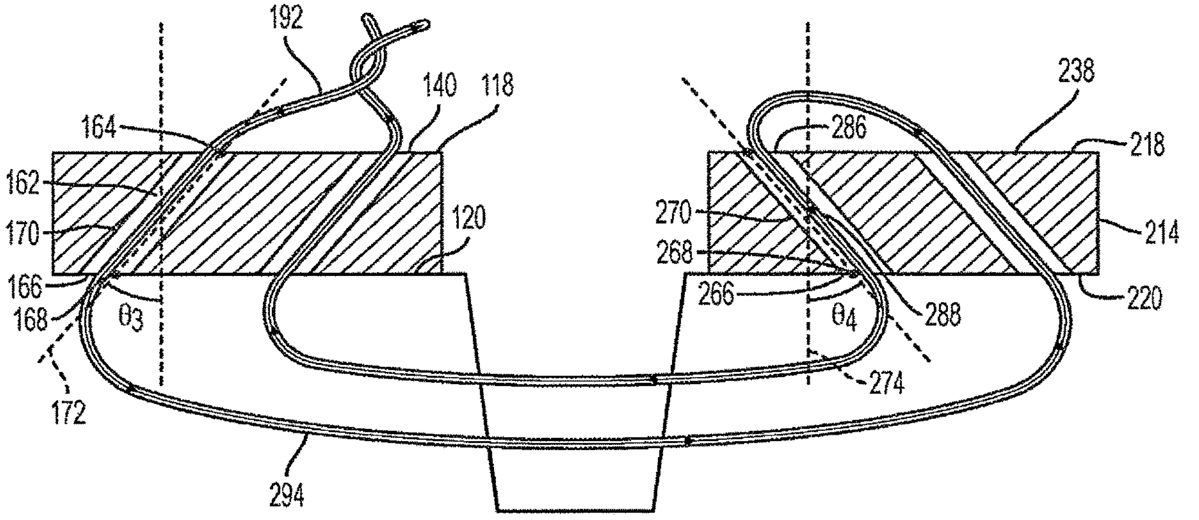
FIG. 3 shows a side section view of one embodiment of the present invention.
Figure 4:
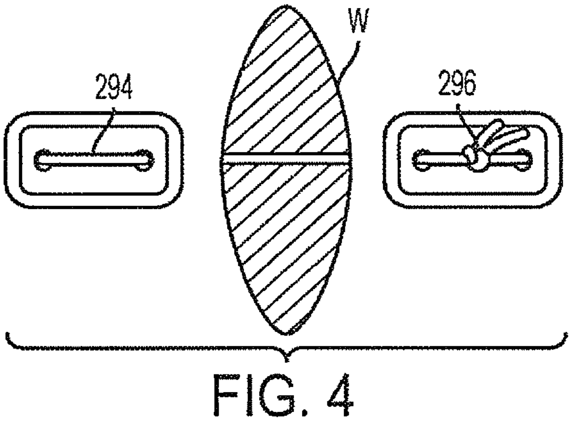
FIG. 4 shows a top view of one embodiment of the present invention.

Turning to FIG. 3 and FIG. 4, and additional tunnel is now added to each plate. A first plate second tunnel 170 is arranged between the first plate upper plane 118 and the first plate lower plane 120. The first plate second tunnel 170 passes through the first plate upper plane second opening center 164 and the first plate lower plane second opening center 168. The first plate second tunnel major axis 172 passes through the first plate upper plane opening second center 164 and the first late lower plane opening second center 168. A third angle θ3 is measured from a first plate second orthogonal axis 162 to the first plate second tunnel major axis 172.

A second plate second tunnel 270 is arranged between the second plate upper plane 228 and the second plate lower plane 220. The second plate second tunnel 270 passes through the second plate upper plane second opening center 264 and the second plate lower plane second opening center 268. The second plate second tunnel major axis 272 passes through the second plate upper plane opening second center 264 and the first late lower plane opening second center 268. A fourth angle θ4 is measured from a second plate second orthogonal axis 274 to the second plate second tunnel major axis 272. A suture 192 is threaded through all of the tunnels and can either be tied or tightened using a machine.

As used in this application a "plate" means a material that does not noticeably deform under a load of five pounds force. In some embodiments, the plate can be made from an auto-clavable polypropylene plastic. As used in this application a "pad" means a material that noticeably deforms under a load of five pounds force. This can include a polyurethane foam that is a medical grade and FDA-approved. The terms "plate" and "pad" are species of a genus that is a "retaining bar" which could be a plate, a pad, or anything functionally equivalent.

Figure 5:
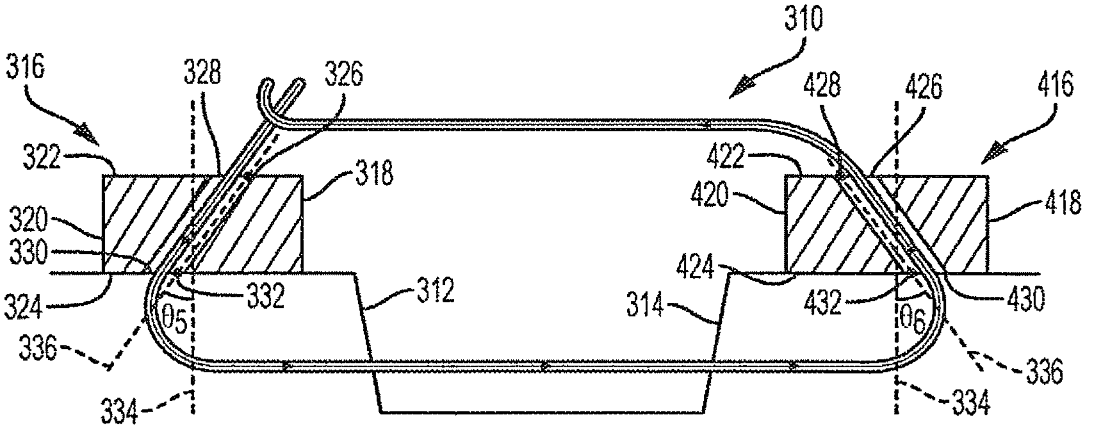
FIG. 5 shows a side section view of one embodiment of the present invention.
Figure 6:
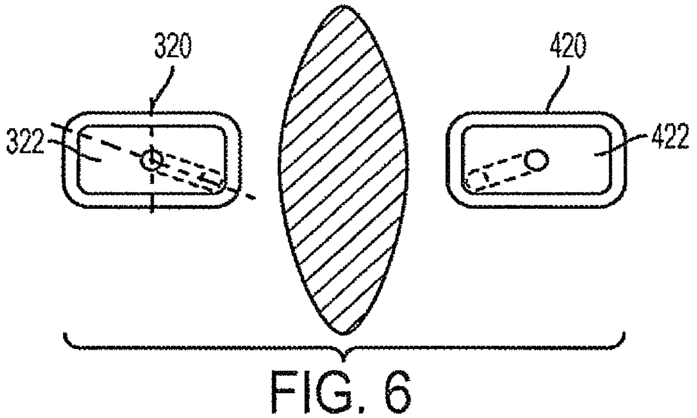
FIG. 6 shows a top view of one embodiment of the present invention.

Turning to FIG. 5 and FIG. 6, a retention suture assembly 310 is adapted to join a first edge 312 to a second edge 314. The retention suture 310 comprises a first suture assembly 316 proximate the first edge 312. The first suture assembly 316 further comprises a first retaining bar 318, further comprising a first retaining bar outer perimeter 320 defining a first retaining bar upper plane 322 and a first retaining bar lower plane 324.

A first retaining bar upper opening 326 further comprises a first retaining bar upper opening center 328 that is arranged within the outer perimeter on the first retaining bar upper plane 322. A first retaining bar lower opening 330 further comprises a first retaining bar lower opening center 332 that is arranged within the outer perimeter on the first retaining bar lower plane 324. A first retaining bar orthogonal axis 334 is orthogonal to the first retaining bar upper plane 322 and the first retaining bar lower plane 324 and travels through the first retaining bar upper opening center 328. A first retaining bar tunnel 330 joins the first retaining bar upper opening 326 and the first retaining bar lower opening 330 wherein a tunnel axis 336 travels through the first retaining bar upper opening center 328 and the first retaining bar lower opening center 332.

A first angle θ5 is measured clockwise from the tunnel axis 336 to the first retaining bar orthogonal axis 334. The first angle θ5 is at least five degrees but no more than one hundred seventy-five degrees. The first retaining bar upper opening center 328 is bisected with an upper plane center line. An upper plane angle is measured clockwise from the upper plane center line to the tunnel axis 336. The upper plane angle can be at least 15 degrees but no more than 165 degrees. In some embodiments, the angle can be about 90 degrees. The figure shows the angle at about 130 degrees.

The retention suture 310 comprises a second suture assembly 416 proximate the second edge 314. The second suture assembly 416 further comprises a second retaining bar 418, further comprising a second retaining bar outer perimeter 420 defining a second retaining bar upper plane 422 and a second retaining bar lower plane 424.

A second retaining bar upper opening 426 further comprises a second retaining bar upper opening center 428 that is arranged within the outer perimeter on the second retaining bar upper plane 422. A second retaining bar lower opening 440 further comprises a second retaining bar lower opening center 442 that is arranged within the outer perimeter on the second retaining bar lower plane 424. A second retaining bar orthogonal axis 444 is orthogonal to the second retaining bar upper plane 422 and the second retaining bar lower plane 424 and travels through the second retaining bar upper opening center 428. A second retaining bar tunnel 440 joins the second retaining bar upper opening 426 and the second retaining bar lower opening 440 wherein a tunnel axis 446 travels through the second retaining bar upper opening center 428 and the second retaining bar lower opening center 442.

A second angle θ6 is measured counter clockwise from the tunnel axis 436 to the second retaining bar orthogonal axis 434. The second angle θ6 is at least five degrees but no more than one hundred seventy-five degrees. A suture 450 is arranged through the first retaining bar tunnel 330 and the second retaining bar tunnel 430 and then tied into a knot 452 above the first edge 312 and the second edge 314. FIG. 4 shows an arrangement where the lower openings are closer together than the upper openings. This has been found to be much less effective than the upper openings being closer together than the lower openings as shown in FIG. 2.

Figure 1:
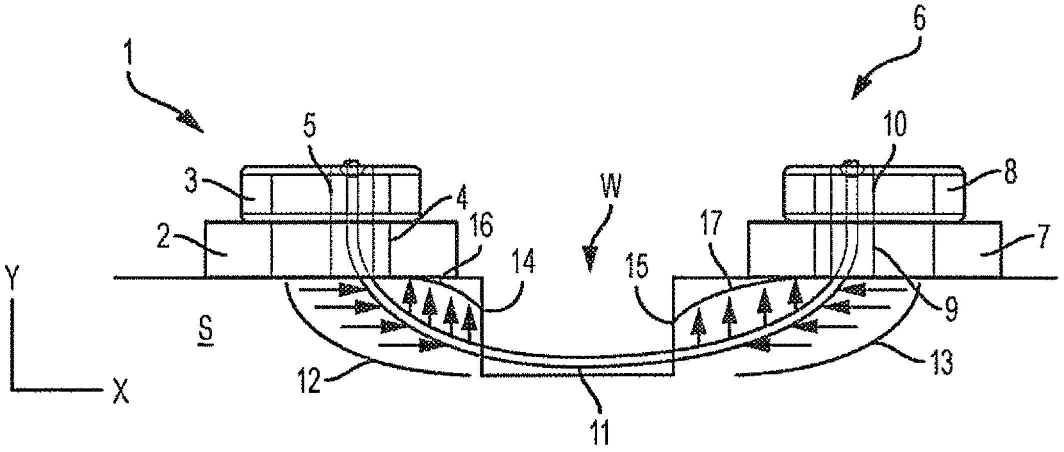
FIG. 1 PRIOR ART
FIG. 1 shows a side section view of one embodiment of a previous endeavor in this field.

FIG. 5, shows one potential theory of why the invention works as well as it does. The suture 194 passes through the first pad second tunnel 170 and the first plate tunnel 130 traveling toward the wound W (not shown). In FIG. 1, Stivala, had the suture distant the walls of the tunnels. The present invention teaches, differently, that the suture 194 should contact the first plate tunnel wall at a first connection point 196. This point incidentally coincides with a first pad orthogonal axis 134, but this centrality is not required. A horizontal closing force 198 Is applied by the suture 194. However, the vertical tearing force 200 is partially offset by a negative vertical force 202 operating in the negative y-direction from the first pad 114.

Figure 8:
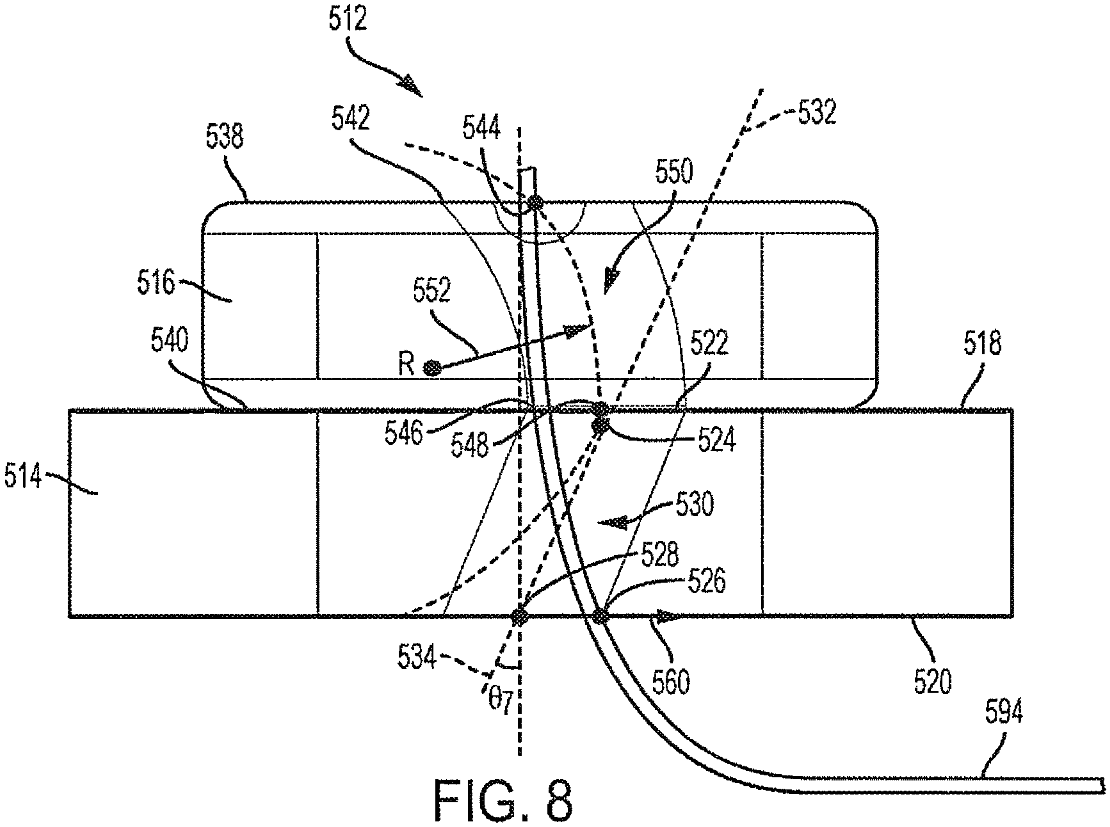
FIG. 8 shows a side section view of one embodiment of the present invention.

FIG. 8 shows another arrangement of an embodiment of the present invention. Here, a first suture assembly 512 contains a first pad 514 adjacent to a first plate 516. The first pad 514 is bound by a first pad upper plane 518 and a first pad lower plane 520. The first pad upper plane 518 further comprises a first pad upper plane opening 522 which has a first pad upper plane opening center 524. Similarly, the first pad lower plane 520 further comprises a first pad lower plane opening 526 which has a first pad lower plane opening center 528. A first pad tunnel 530 exists between the first pad lower plane opening 126 and the first pad upper plane opening 122. A first pad tunnel major axis 532 passes through the first pad upper plane opening center 524 and the first pad lower plane opening center 528. For reference, a first pad orthogonal axis 534 passes through the first pad upper plane opening center 524 orthogonal to the first pad upper plane 518 and the first pad lower plane 520. A first pad angle θ7 is measured clockwise from the first pad orthogonal axis 534 to the first pad tunnel major axis 532.

The first plate 516 is bound by a first plate upper plane 538 and a first plate lower plane 540. The first plate upper plane 138 further comprises a first plate upper plane opening 542 which has a first plate upper plane opening center 544. Similarly, the first plate lower plane 540 further comprises a first plate lower plane opening 546 which has a first plate lower plane opening center 548. A first plate tunnel 550 exists between the first plate lower plane opening 546 and the first plate upper plane opening 542. A first plate tunnel radius 552 passes through the first plate upper plane opening center 544 and the first plate lower plane opening center 548.

Figure 7:
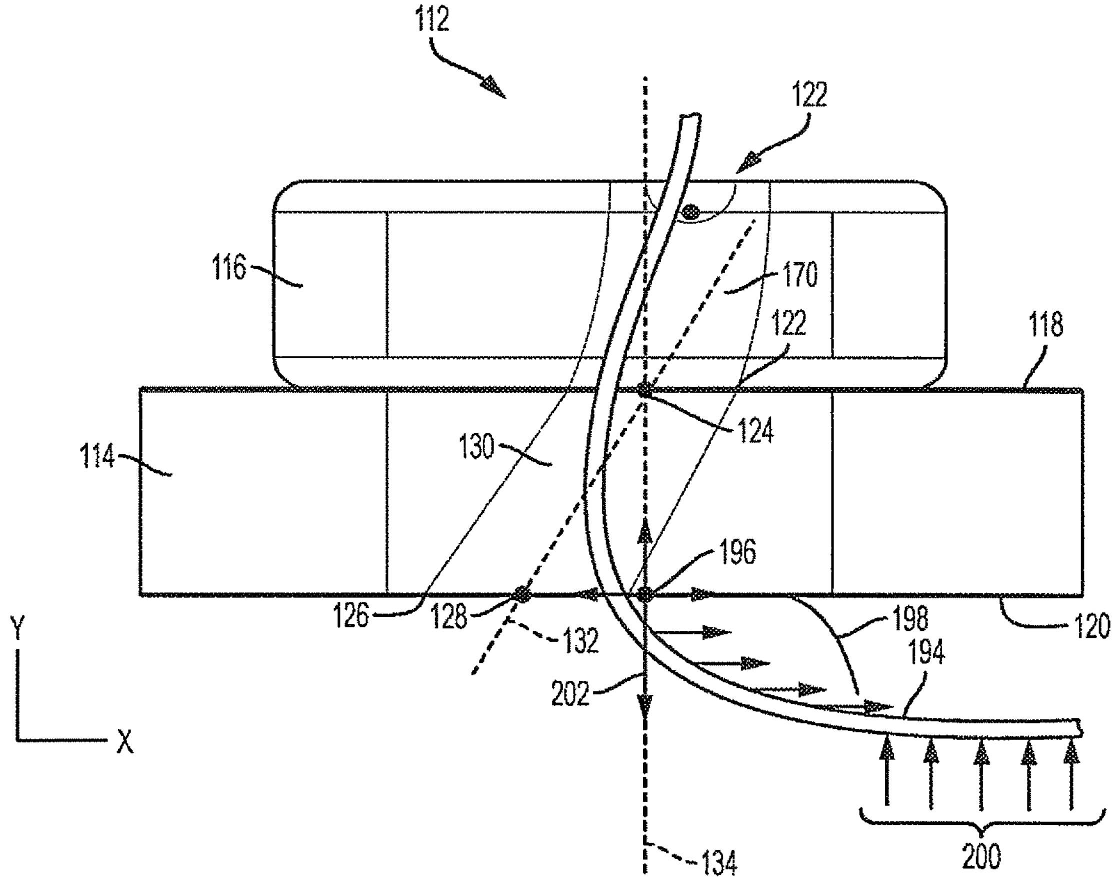
FIG. 7 shows a side section view of one embodiment of the present invention.

Comparing FIG. 6 to FIG. 8, the first plate tunnel radius 152 is much larger than and the first plate tunnel radius 552. This causes the suture 594 to distribute an increased amount of force into a side wall of the first pad tunnel 530. The horizontal force 560 is not distributed higher on the side wall of the first pad tunnel 530 than it was in FIG. 7.

Figure 9:
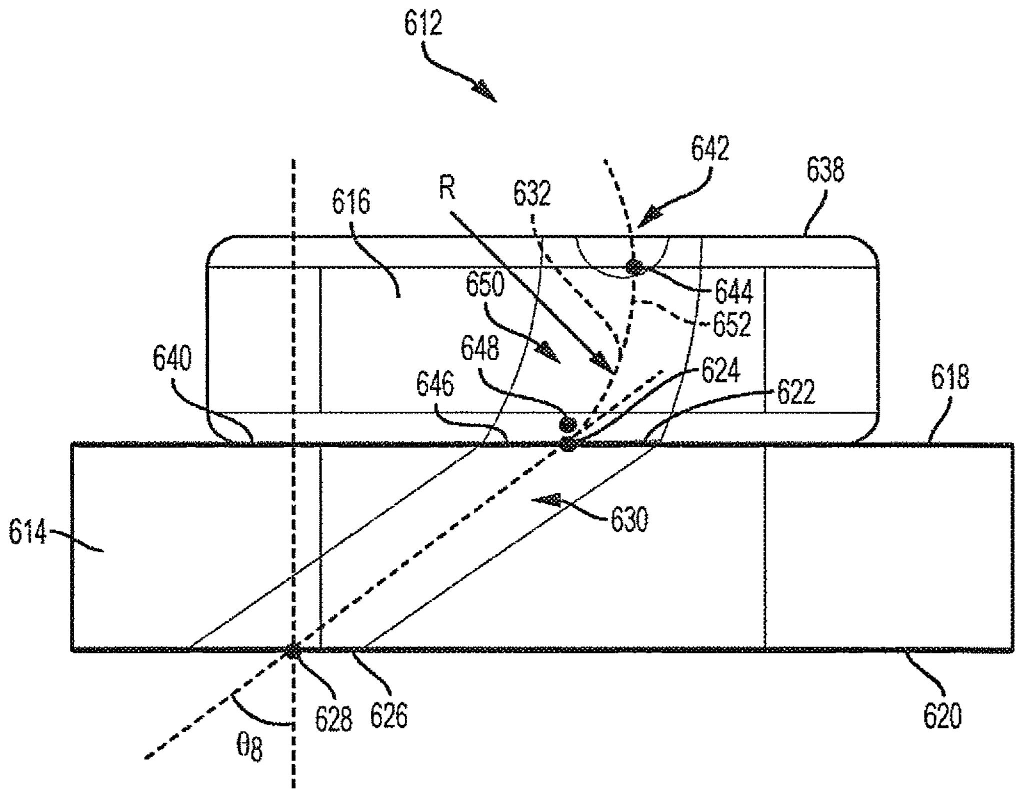
FIG. 9 shows a side section view of one embodiment of the present invention.

FIG. 9 shows another arrangement of an embodiment of the present invention. Here, a first suture assembly 612 contains a first pad 614 adjacent to a first plate 616. The first pad 614 is bound by a first pad upper plane 618 and a first pad lower plane 620. The first pad upper plane 618 further comprises a first pad upper plane opening 622 which has a first pad upper plane opening center 624. Similarly, the first pad lower plane 620 further comprises a first pad lower plane opening 626 which has a first pad lower plane opening center 628. A first pad tunnel 630 exists between the first pad lower plane opening 626 and the first pad upper plane opening 622. A first pad tunnel major axis 632 passes through the first pad upper plane opening center 624 and the first pad lower plane opening center 628. For reference, a first pad orthogonal axis 634 passes through the first pad lower plane opening center 628 orthogonal to the first pad upper plane 618 and the first pad lower plane 620. A first pad angle θ8 is measured clockwise from the first pad orthogonal axis 534 to the first pad tunnel major axis 532.

The first plate 616 is bound by a first plate upper plane 638 and a first plate lower plane 640. The first plate upper plane 638 further comprises a first plate upper plane opening 642 which has a first plate upper plane opening center 644. Similarly, the first plate lower plane 640 further comprises a first plate lower plane opening 646 which has a first plate lower plane opening center 648. A first plate tunnel 650 exists between the first plate lower plane opening 646 and the first plate upper plane opening 642. A first plate tunnel radius 652 passes through the first plate upper plane opening center 644 and the first plate lower plane opening center 648.

In this example, the first pad angle θ8 is substantially larger than that the first pad angle θ7. This simply causes forces to be distributed differently within the first suture assembly 612.

Figure 10:
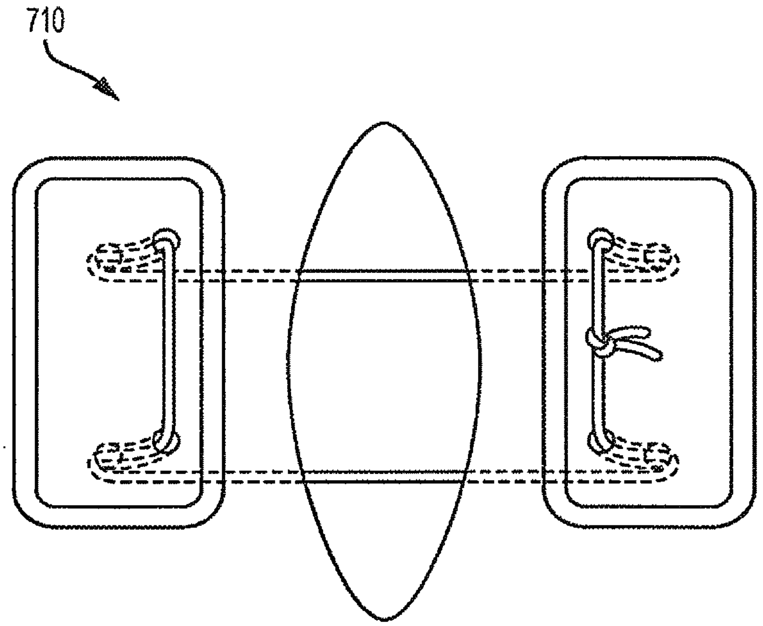
FIG. 10 shows a top view of one embodiment of the present invention.
Figure 11:
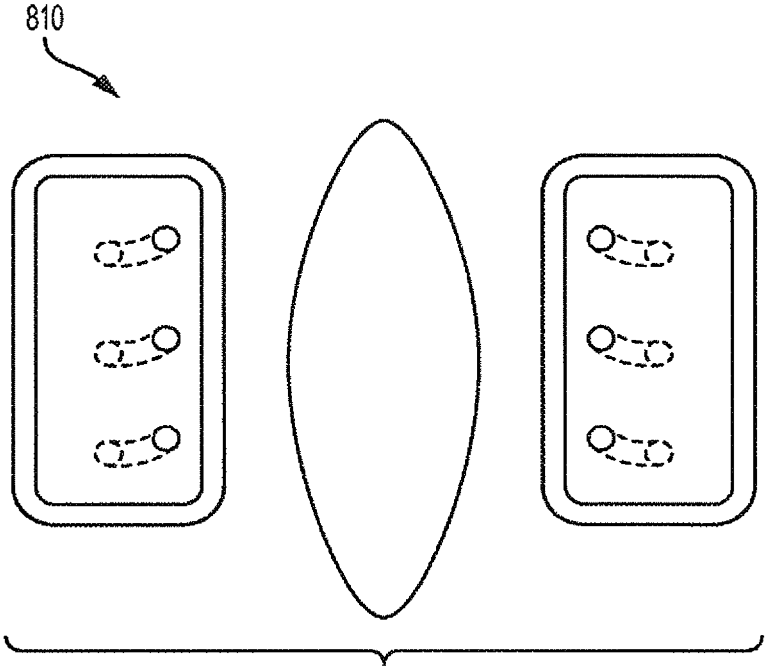
FIG. 11 shows a top view of one embodiment of the present invention.
Figure 12:
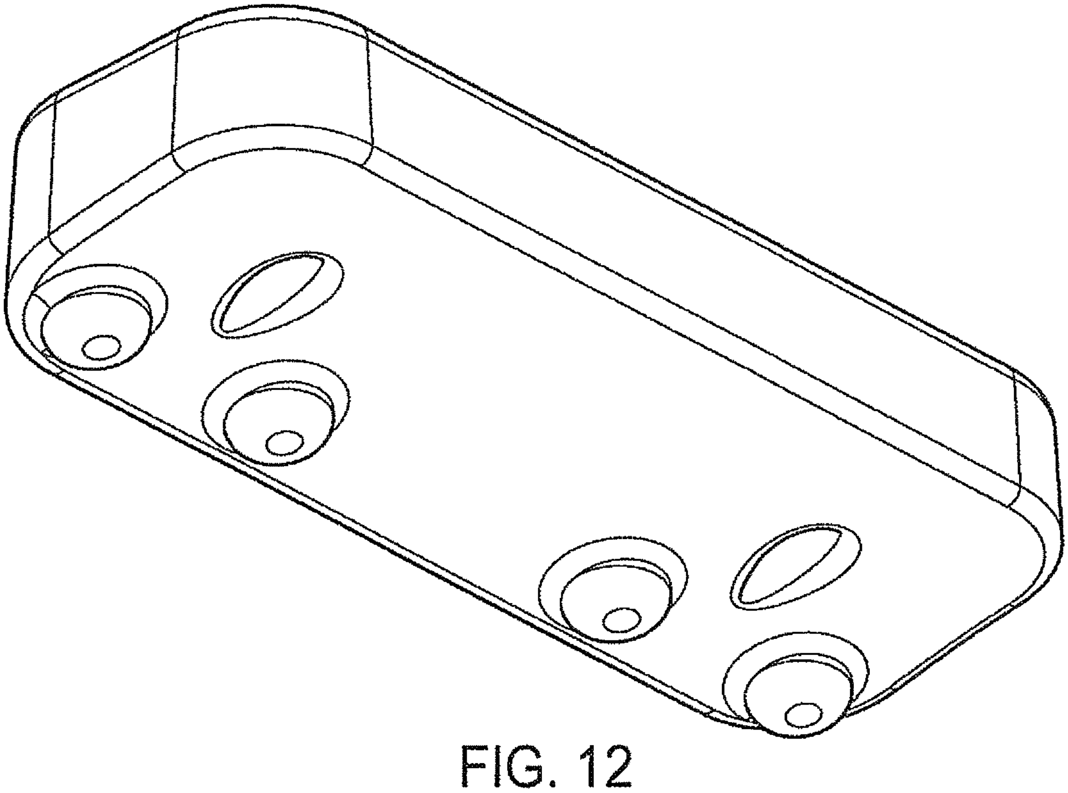
FIG. 12 shows a perspective view of one embodiment of the present invention.
Figure 13:
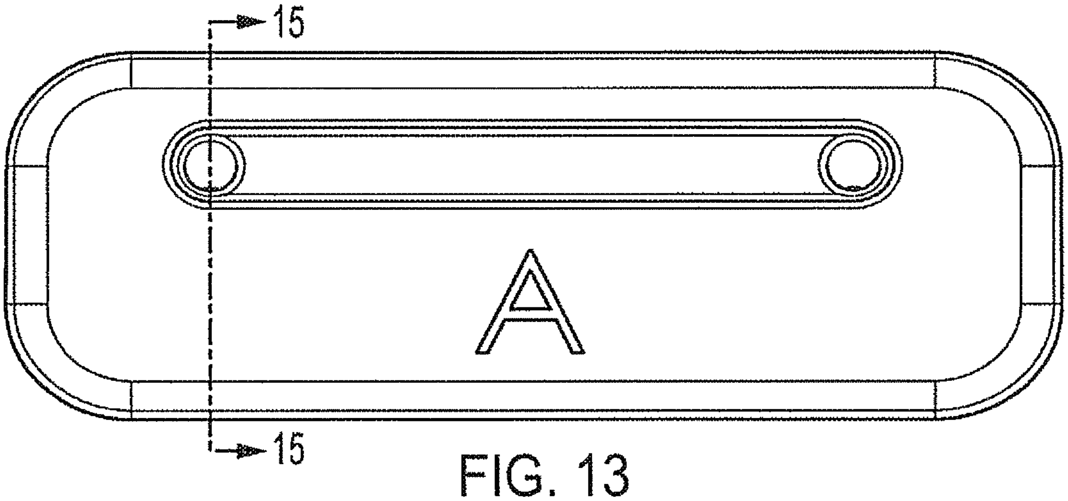
FIG. 13 shows a top view of one embodiment of the present invention.
Figure 14:
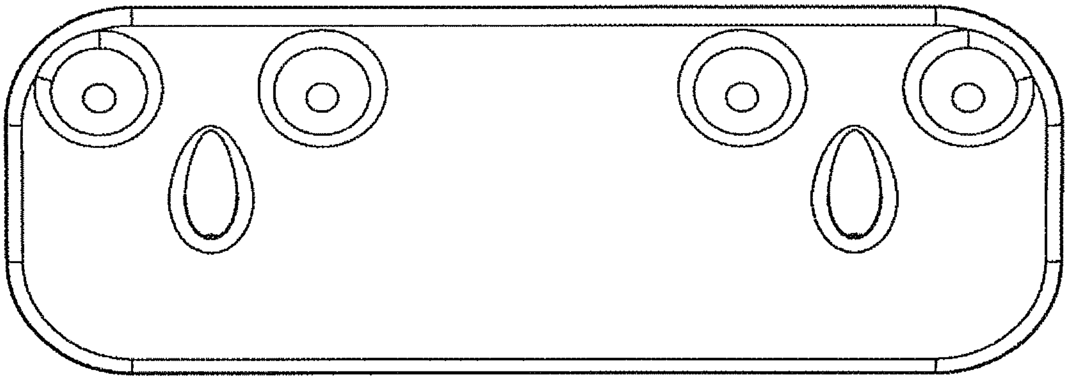
FIG. 14 shows a perspective view of one embodiment of the present invention.
Figure 15:
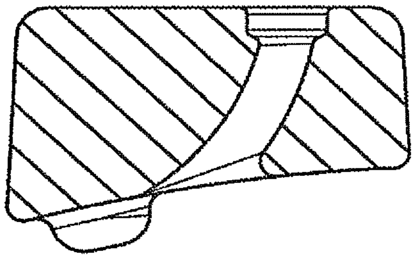
FIG. 15 shows a section view of one embodiment of the present invention taken along line 15-15 in FIG. 13.
Figure 16:
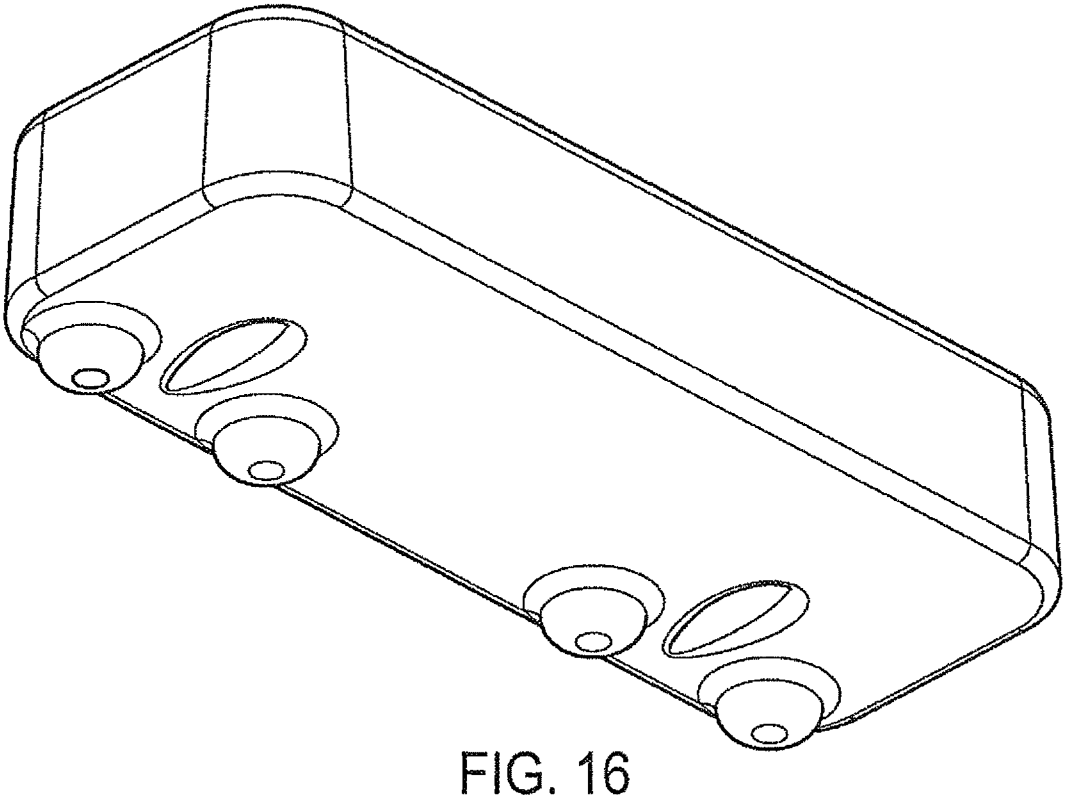
FIG. 16 shows a perspective view of one embodiment of the present invention.
Figure 17:
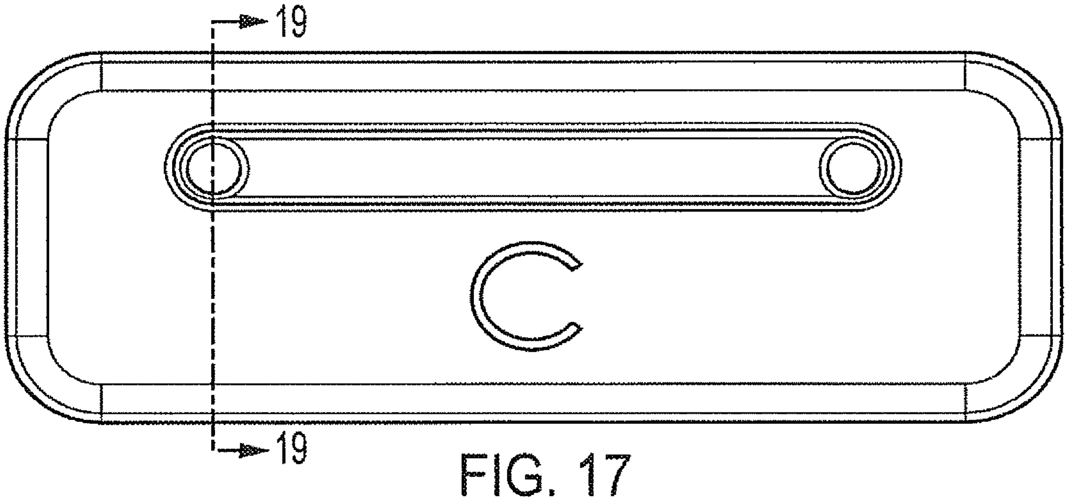
FIG. 17 shows a top view of one embodiment of the present invention.
Figure 18:
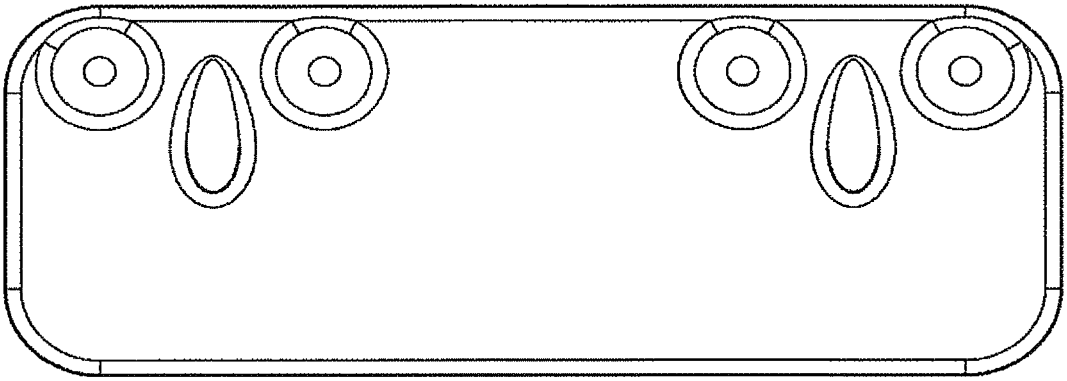
FIG. 18 shows a perspective view of one embodiment of the present invention.
Figure 19:
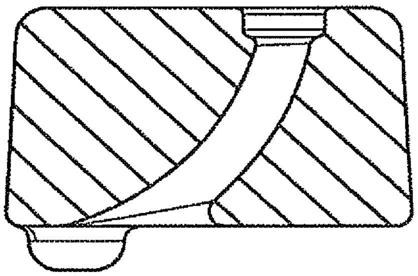
FIG. 19 shows a section view of one embodiment of the present invention taken along line 19-19 in FIG. 17.
Figure 20:
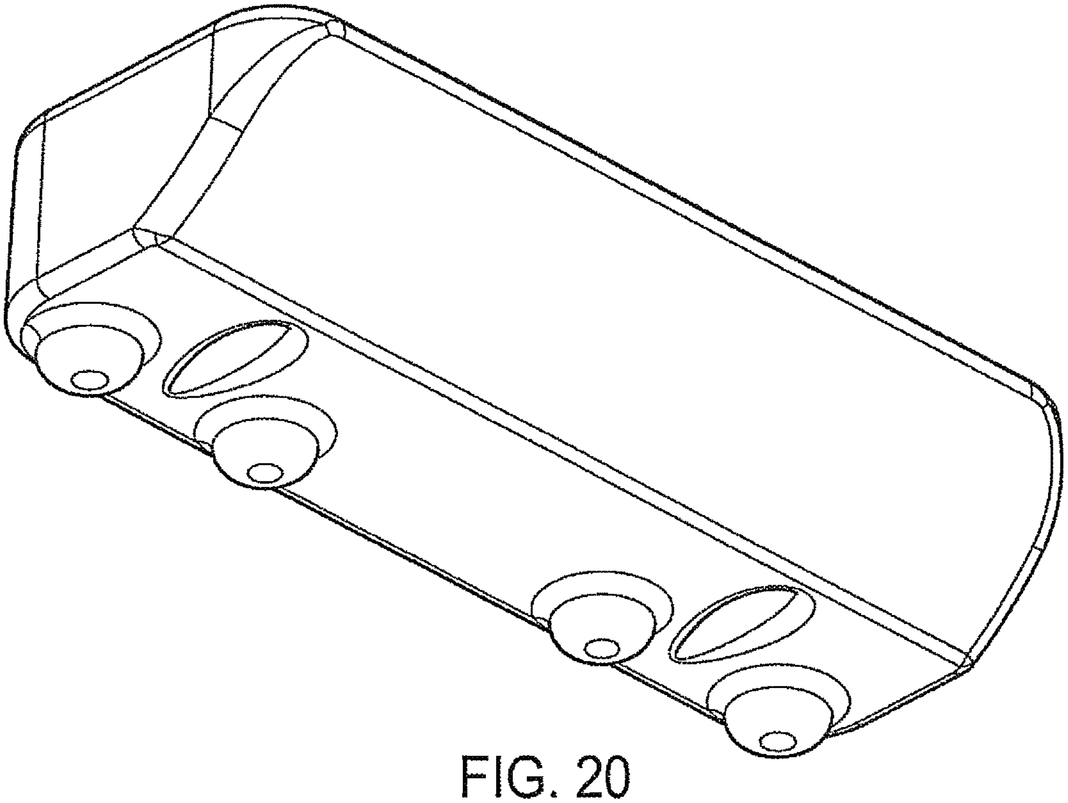
FIG. 20 shows a perspective view of one embodiment of the present invention.
Figure 21:
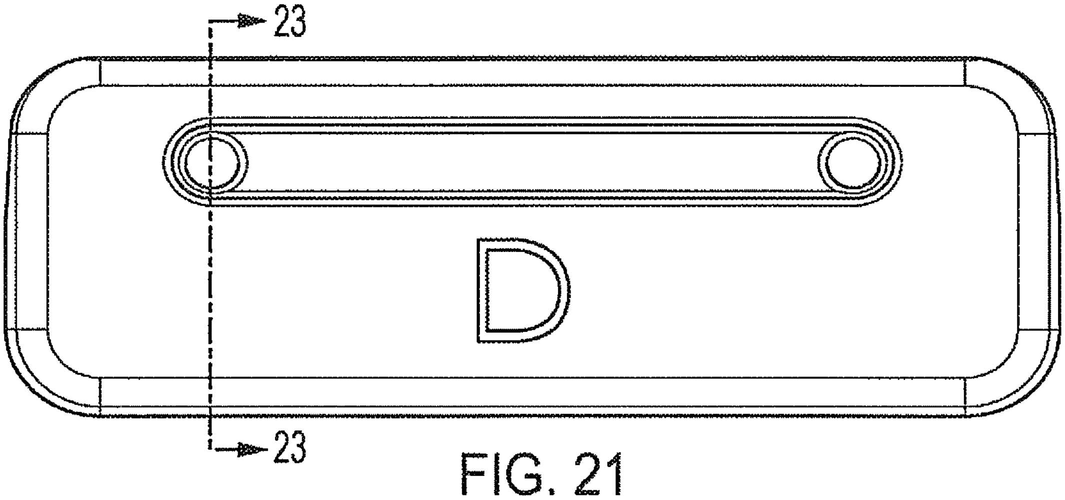
FIG. 21 shows a top view of one embodiment of the present invention.
Figure 22:
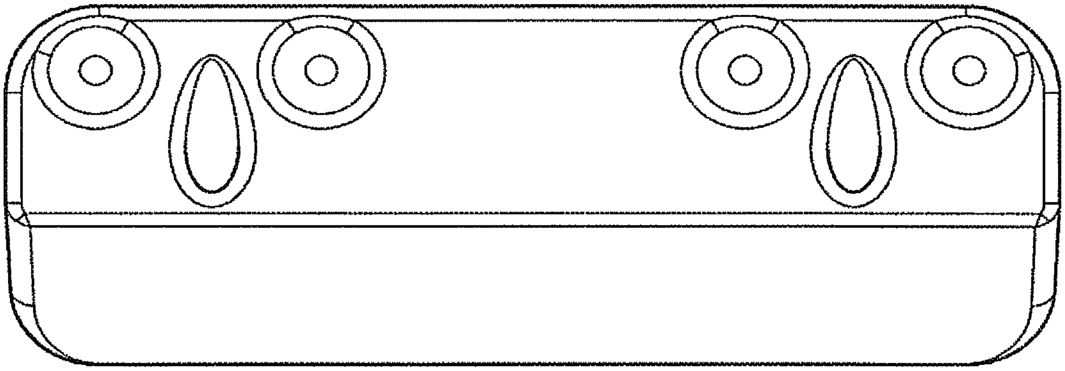
FIG. 22 shows a perspective view of one embodiment of the present invention.
Figure 23:
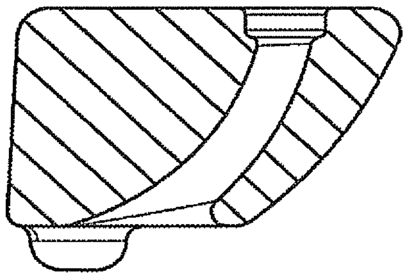
FIG. 23 shows a section view of one embodiment of the present invention taken along line 23-23 in FIG. 21.
Figure 24:
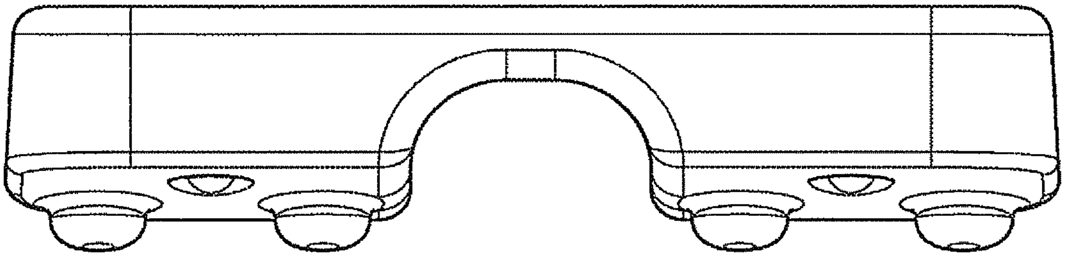
FIG. 24 shows a front perspective view of one embodiment of the present invention.
Figure 25:
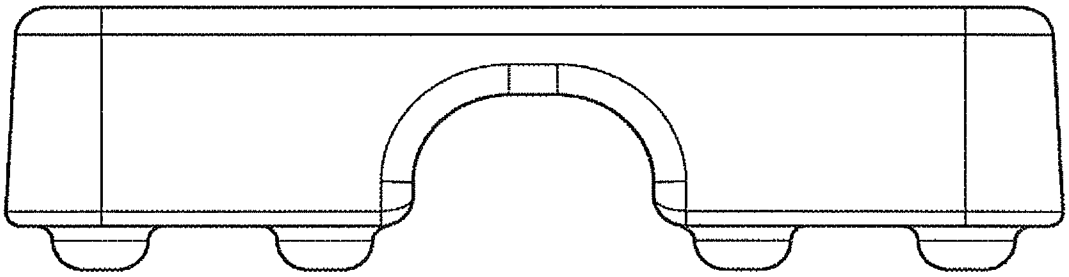
FIG. 25 shows a front view of one embodiment of the present invention.
Figure 26:
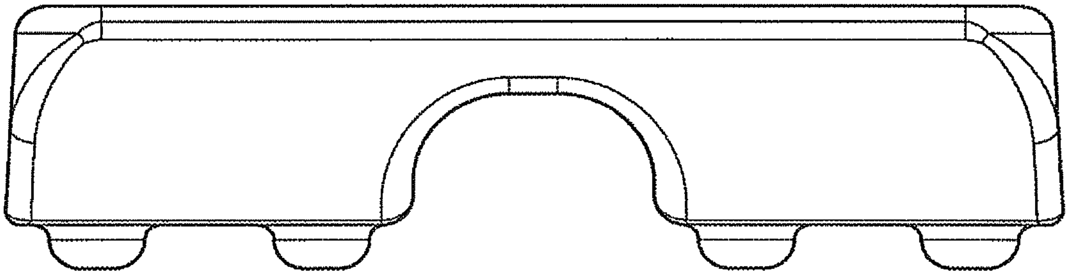
FIG. 26 shows a rear view of one embodiment of the present invention.
Figure 27:
FIG. 27 shows a front perspective view of one embodiment of the present invention.
Figure 28:
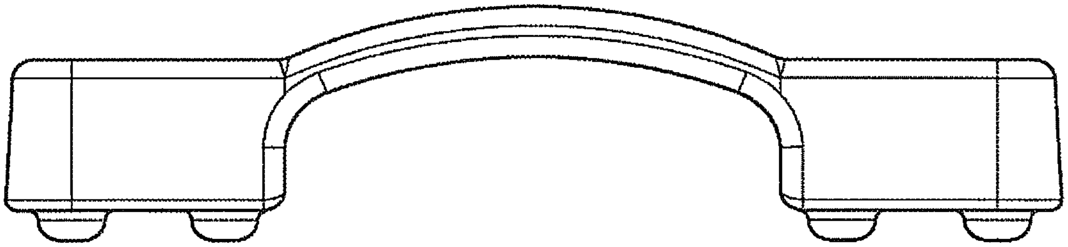
FIG. 28 shows a front view of one embodiment of the present invention.
Figure 29:
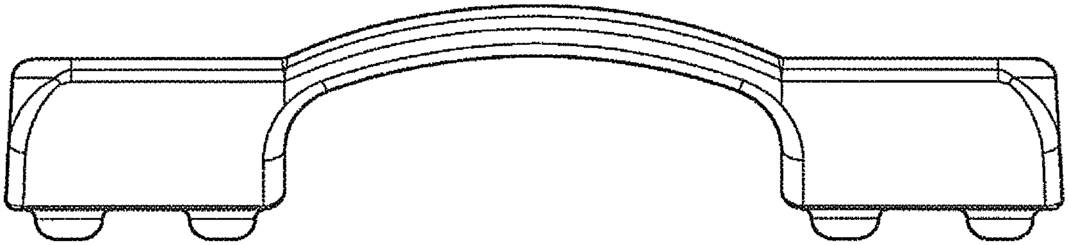
FIG. 29 shows a rear view of one embodiment of the present invention.

In FIG. 10, retention suture assembly 710 uses two tunnels on each pad that are approximately parallel to one another. In FIG. 11, three tunnels are shown.

As stated above, a retention suture assembly 110 is adapted to join a pair of edges from a wound. The retention suture assembly 110 comprises a first suture assembly 112, arranged proximate a first edge and a second suture assembly 212 arranged proximate a second edge.

Figure 30:
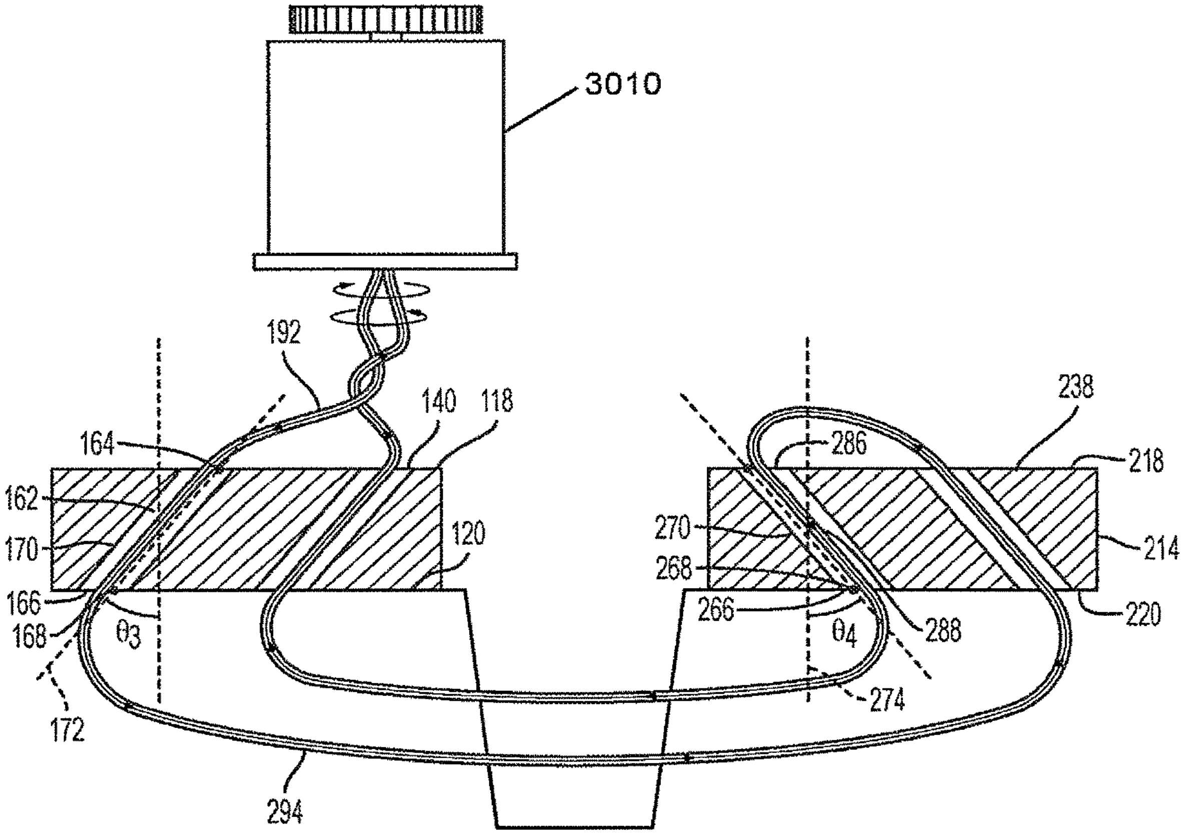
FIG. 30 shows side section view of one embodiment of the present invention shown in use.
Figure 31:
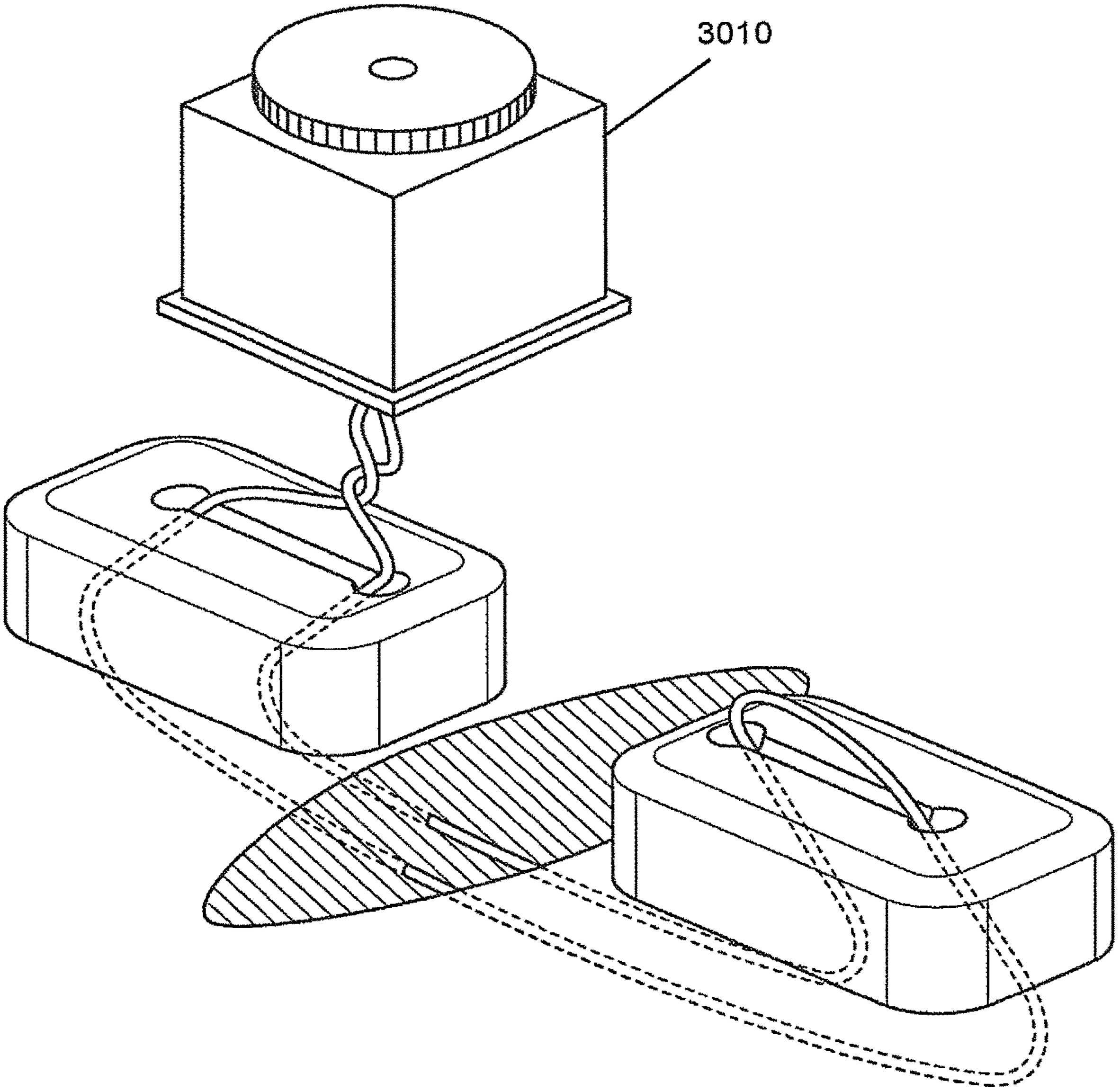
FIG. 31 shows perspective view of one embodiment of the present invention shown in use.

Turning to FIGS. 30-31, the first suture assembly 110 further comprises a first retaining bar, further comprising a first retaining bar outer perimeter, a first retaining bar upper plane and a first retaining bar lower plane. A first retaining bar upper opening further comprises a first retaining bar upper opening center and a first retaining bar lower opening further comprises a first retaining bar lower opening center. The first retaining bar lower opening center is relatively distant the first edge and the first retaining bar upper opening center is relatively proximate the first edge. A second suture assembly can be similarly arranged.

A suture 192 joins the first suture assembly and the second suture assembly under tension. In some embodiments, the suture is tied into a knot 296 as shown in FIG. 4. In other embodiments, the suture is tightened with a tensioning device 3010 as is shown in FIGS. 30 and 31.

In some embodiments shown in FIGS. 30 and 31 an upper linear distance measured from the first retaining bar upper opening center to the second retaining bar upper opening center is less than a lower liner distance measured from the first retaining bar lower opening center to the second retaining bar lower opening center. The first suture assembly further comprises a first retaining bar tunnel, joining the first retaining bar upper opening and the first retaining bar lower opening. The first retaining bar tunnel further comprises a first retaining bar side wall. The second suture assembly further comprises a second retaining bar tunnel, joining the second retaining bar upper opening and the second retaining bar lower opening; wherein the second retaining bar tunnel further comprises a second retaining bar side wall. It follows that the suture is arranged through the first retaining bar tunnel such that the suture contacts the first retaining bar side wall distributing some of a force from the suture into the first retaining bar; the suture further arranged through the second retaining bar tunnel such that the suture contacts the second retaining bar side wall distributing some of the force from the suture into the second retaining bar pulling the first retaining bar to the second retaining bar.

A first retaining bar orthogonal axis, that is orthogonal to the first retaining bar upper plane and the first retaining bar lower plane, travels through the first retaining bar upper opening center. A first retaining bar tunnel axis travels through the first retaining bar upper opening center and the first retaining bar lower opening center. A first angle is measured clockwise from the tunnel axis to the first retaining bar orthogonal axis. The first angle is at least five degrees but no more than one hundred seventy-five degrees angled toward the first edge.

Similarly, a second retaining bar orthogonal axis, that is orthogonal to the second retaining bar upper plane and the second retaining bar lower plane, travels through the second retaining bar upper opening center. A second retaining bar tunnel axis travels through the second retaining bar upper opening center and the second retaining bar lower opening center. A second angle is measured counter clockwise from the tunnel axis to the second retaining bar orthogonal axis; wherein the second angle is at least five degrees but no more than one hundred seventy-five degrees angled toward the second edge.

A first retaining bar second upper opening further comprising a first retaining bar second upper opening center and a first retaining bar second lower opening further comprising a first retaining bar second lower opening center. The first retaining bar second lower opening center is relatively distant the first edge and the first retaining bar second upper opening center is relatively proximate the first edge.

A first retaining bar upper channel arranged into the first retaining bar upper plane and connecting the first retaining bar upper opening to the first retaining bar second upper opening; wherein the first retaining bar upper channel further comprises a first retaining bar upper channel central axis A first retaining bar central opening, spanning two sides of the first retaining bar outer perimeter creating a first retaining bar lower tunnel having a first retaining bar lower tunnel central axis wherein the first retaining bar upper channel central axis is approximately perpendicular to the first retaining bar lower tunnel central axis.

As shown in FIGS. 12-23, a first foot extends from the first retaining bar lower plane between a first retaining bar first edge and the first retaining bar lower opening. A second foot extends from the first retaining bar lower plane between the first retaining bar lower opening and the first retaining bar central opening. A third foot extends from the first retaining bar lower plane between the first retaining bar central opening and the first retaining bar second opening. A fourth foot extends from the first retaining bar lower plane between the first retaining bar second opening and a first retaining bar second edge.

Turning to FIGS. 24-29, a central portion exists between the second foot and the third foot. In some embodiments the central portion is arched away from the second foot and the third foot in a concave manner. In some embodiments this arch makes the first retaining bar upper plane convex. In other embodiments, the arch does not affect the first retaining bar upper plane. In some embodiments a through connects the first retaining bar upper plane central opening and the second retaining bar upper plane central opening.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, 16. In particular, any use of "step of" in the claims is not intended to invoke the provision of 35 U.S.C. § 112, 16.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A retention suture assembly, adapted to join a pair of edges from a wound; the retention suture assembly comprising:
- a first suture assembly, arranged proximate a first edge and further comprising:
  - a first retaining bar, further comprising a first retaining bar outer perimeter,
  - a first retaining bar upper plane and a first retaining bar lower plane;
  - a first retaining bar upper opening further comprising a first retaining bar upper opening center and a first retaining bar lower opening further comprising a first retaining bar lower opening center;
- a second suture assembly, arranged proximate a second edge and further comprising:
  - a second retaining bar, further comprising a second retaining bar outer perimeter, a second retaining bar upper plane and a second retaining bar lower plane;
  - a second retaining bar upper opening further comprising a second retaining bar upper opening center and a second retaining bar lower opening further comprising a second retaining bar lower opening center;
  - wherein the first retaining bar lower plane includes a pair of first feet extending therefrom and separated by a portion of the first retaining bar lower plane, each of the pair of first feet positioned adjacent to the first retaining bar lower opening, and further
  - wherein the second retaining bar lower plane includes a pair of second feet extending therefrom and separated by a portion of the second retaining bar lower plane, each of the pair of second feet positioned adjacent to the second retaining bar lower opening.

2. The retention suture assembly of claim 1, wherein an upper linear distance measured from the first retaining bar upper opening center to the second retaining bar upper opening center is less than a lower liner distance measured from the first retaining bar lower opening center to the second retaining bar lower opening center.

3. The retention suture assembly of claim 1, the first suture assembly further comprising a first retaining bar tunnel, joining the first retaining bar upper opening and the first retaining bar lower opening; wherein the first retaining bar tunnel further comprises a first retaining bar side wall.

4. The retention suture assembly of claim 3, the second suture assembly further comprising a second retaining bar tunnel, joining the second retaining bar upper opening and the second retaining bar lower opening; wherein the second retaining bar tunnel further comprises a second retaining bar side wall.

5. The retention suture assembly of claim 4, further comprising a suture, joining the first suture assembly and the second suture assembly under tension, wherein the suture is arranged through the first retaining bar tunnel such that the suture contacts the first retaining bar side wall distributing some of a force from the suture into the first retaining bar; the suture further arranged through the second retaining bar tunnel such that the suture contacts the second retaining bar side wall distributing some of the force from the suture into the second retaining bar pulling the first retaining bar to the second retaining bar.

6. The retention suture assembly of claim 4, further comprising:

a first retaining bar orthogonal axis that is orthogonal to the first retaining bar upper plane and the first retaining bar lower plane and travels through the first retaining bar upper opening center;

a first retaining bar tunnel axis, traveling through the first retaining bar upper opening center and the first retaining bar lower opening center;

a first angle, measured clockwise from the tunnel axis to the first retaining bar orthogonal axis; wherein the first angle is at least five degrees but no more than one hundred seventy-five degrees angled toward the first edge.

7. The retention suture assembly of claim 6, further comprising:

a second retaining bar orthogonal axis that is orthogonal to the second retaining bar upper plane and the second retaining bar lower plane and travels through the second retaining bar upper opening center;

a second retaining bar tunnel axis, traveling through the second retaining bar upper opening center and the second retaining bar lower opening center;

a second angle, measured counter clockwise from the tunnel axis to the second retaining bar orthogonal axis; wherein the second angle is at least five degrees but no more than one hundred seventy-five degrees angled toward the second edge.

8. The retention suture assembly of claim 1, wherein the first retaining bar lower opening center is relatively distant the first edge and the first retaining bar upper opening center is relatively proximate the first edge; and wherein the second retaining bar lower opening center is relatively distant the second edge and the second retaining bar upper opening center is relatively proximate the second edge.

* * * * *